(12) United States Patent
Prochazka (10) Patent No.: US 6,961,623 B2
(45) Date of Patent: Nov. 1, 2005

(54) METHOD AND APPARATUS FOR CONTROLLING A DEVICE OR PROCESS WITH VIBRATIONS GENERATED BY TOOTH CLICKS

(75) Inventor: Arthur Prochazka, Edmonton (CA)

(73) Assignee: Rehabtronics Inc., Edmonton (CA)

( * ) Notice: Subject to any disclaimer, the term of this patent is extended or adjusted under 35 U.S.C. 154(b) by 0 days.

(21) Appl. No.: 10/688,865

(22) Filed: Oct. 17, 2003

(65) Prior Publication Data

US 2004/0130455 A1 Jul. 8, 2004

Related U.S. Application Data

(60) Provisional application No. 60/421,633, filed on Oct. 25, 2002, and provisional application No. 60/419,393, filed on Oct. 17, 2002.

(51) Int. Cl.[7] ............................................... G05B 15/00
(52) U.S. Cl. ........................................... 700/1; 600/595
(58) Field of Search ................... 700/1; 340/825.71; 600/586–587, 590, 595, 300

(56) References Cited

U.S. PATENT DOCUMENTS

| | | | | |
|---|---|---|---|---|
| 3,896,817 A | * | 7/1975 | Hursen et al. ................. | 607/42 |
| 4,207,959 A | | 6/1980 | Youdin et al. ............... | 180/167 |
| 4,392,244 A | * | 7/1983 | Yoshizawa et al. ........... | 455/79 |
| 4,558,704 A | * | 12/1985 | Petrofsky ..................... | 607/48 |
| 4,629,424 A | | 12/1986 | Lauks et al. ................... | 433/6 |

(Continued)

FOREIGN PATENT DOCUMENTS

| | | | | |
|---|---|---|---|---|
| GB | 1150125 | 4/1969 | ............ | H04B/7/00 |
| GB | 2236874 | 4/1991 | ........... | G06F/3/033 |
| GB | 2254677 | 10/1992 | ............. | G06F/3/02 |
| WO | WO 02/07151 | 7/2001 | ........... | G10L/21/00 |
| WO | WO 2004/056298 | 11/2002 | ........... | A61F/11/06 |
| WO | WO 2004/068464 | 1/2004 | ........... | H04R/25/00 |

OTHER PUBLICATIONS

Crago, P. E., Peckham, P. H., Mansour, J. M., Lan, N., Kilgore, K. and Chizeck, H. J. (1991) "II. Control of Neuroprostheses." In "Functional Neuromuscular Stimulation for Restoration of Hand Grasp." 8th Progress Report, NIH Contract NO1–NS–9–2356, 19–23. Case Western University & MetroHealth Medical Center. Sep. 1991.

(Continued)

*Primary Examiner*—Anthony Knight
*Assistant Examiner*—Ronald D Hartman, Jr.
(74) *Attorney, Agent, or Firm*—Christensen O'Connor Johnson Kindness PLLC (57) ABSTRACT

A method and apparatus for use in controlling a device or process. The first step of the method involves attaching a detector (20) adapted to detect mechanical vibrations to a person's head (22). A second step involves detecting mechanical vibrations elicited by sudden contact of upper teeth (24) and lower teeth (26). A third step involves using the mechanical vibrations to trigger a signal to control operation of a device or process (36, 80, 82, 84, 86, 88, 90).

42 Claims, 7 Drawing Sheets

U.S. PATENT DOCUMENTS

| | | | |
|---|---|---|---|
| 4,865,610 A | | 9/1989 | Muller .......................... 623/24 |
| 5,054,079 A | | 10/1991 | Frielingsdorf et al. ....... 381/151 |
| 5,212,476 A | * | 5/1993 | Maloney ................. 340/825.19 |
| 5,233,662 A | | 8/1993 | Christensen .................. 387/70 |
| 5,341,133 A | * | 8/1994 | Savoy et al. ................... 341/22 |
| 5,523,745 A | | 6/1996 | Fortune et al. ......... 340/825.19 |
| 5,533,519 A | * | 7/1996 | Radke et al. ................ 600/595 |
| 5,562,707 A | | 10/1996 | Prochazka et al. ............. 607/2 |
| 5,689,246 A | | 11/1997 | Dordick et al. ......... 340/825.19 |
| 5,730,151 A | | 3/1998 | Summer et al. ............. 128/777 |
| 5,812,978 A | | 9/1998 | Nolan ......................... 704/275 |
| 5,989,023 A | | 11/1999 | Summer et al. .............. 433/69 |
| 6,107,922 A | | 8/2000 | Bryuzgin .................... 340/576 |
| 6,222,524 B1 | | 4/2001 | Salem et al. ................. 345/157 |
| 6,463,157 B1 | | 10/2002 | May ........................... 381/151 |
| 2002/0039425 A1 | | 4/2002 | Burnett et al. .............. 381/94.7 |
| 2002/0099541 A1 | | 7/2002 | Burnett ....................... 704/223 |
| 2002/0143242 A1 | * | 10/2002 | Nemirovski ................ 600/300 |
| 2002/0198705 A1 | | 12/2002 | Burnett ....................... 704/214 |
| 2003/0120183 A1 | * | 6/2003 | Simmons .................... 600/595 |
| 2003/0128848 A1 | | 7/2003 | Burnett ...................... 381/71.8 |
| 2003/0179888 A1 | | 9/2003 | Burnett et al. ............. 381/71.8 |
| 2003/0228023 A1 | | 12/2003 | Burnett et al. ................ 381/92 |

OTHER PUBLICATIONS

Crago, P. E., Peckham, P. H. Mansour, J. M., Lan, N., Kilgore, K. and Chizeck, H. J. (1991). "II. Control of Neuroprostheses." In "Functional neuromuscular stimulation for restoration of hand grasp." $7^{th}$ Progress Report, NIH Contract NoI–NS–9–2356, 26–34. Case Western University & MetroHealth Medical Center. Jun. 1991.

Crago, P. E., Peckham, P. H. Mansour, J. M., Lan, N., Kilgore, K. and Chizeck, H. J. (1992). "IIA. Command Control of FNS Grasp Using Wrist Position." In "Functional neuromuscular stimulation for restoration of hand grasp." $11^{th}$ Progress Report, NIH Contract NoI–NS–9–2356, 9–12. Case Western University & MetroHealth Medical Center. Jun. 1992.

Handa, Y., Itchie, M., Handa, T., Takahashi, K. Saito, C., Kameyama, J. & Hoshimiya, N. (1989) "FES–control of multijoint system in the paralysed upper limb." Osaka Int. Workshop on FNS. pp. 91–95, Nov. 19, 1989.

Liberson W.T., Holmquest H.J. Scott D, Dow, M.(1961) Functional electrotherapy: stimulation of the peroneal nerve synchronized with the swing phase of the gait of hemiplegic patients. Archives of Physical and Medical Rehabilitation 42: 101–105.

Peckham, P.K. and Kilgore, K. (1991) "II. Control of Neuroprostheses." In "Functional Neuromuscular Stimulation for Restoration of Hand Grasp." $9^{th}$ Progress Report, NIH Contract NO1–NS–9–2356, 38–48. Case Western University & MetroHealth Medical Center. Dec. 1991.

Peckham, P.K. Kilgore, K. (1992) "Evaluation of the Influence of Electrode Recruitment Properties on FNS Grasp Output." In "Functional Neuromuscular Stimulation for Restoration of Hand Grasp." $10^{th}$ Progress Report, NIH Contract NO1–NS–9–2356, 2. Case Western University & MetroHealth Medical Center. Mar. 1992.

Peckham, P. K, Marsolais, E. B. & Mortimer, J. T. (1980) Restoration of key grip and release in the C6 tetraplegic patient through functional electrical stimulation. J. Hand Surgery, 5(5), 462–469.

Peckham, P. H. & Keith, M. W. (1992) "Motor prostheses for restoration of upper extremity function" In "Neural Prostheses: Replacing Motor Function After Disease or Disability" eds.: Stein, R. B., Peckham, P. H. & Popovic, D. B. New York: Oxford University Press.

Prochazka, A. & Wiles, C. M. (1983) "Electrical stimulation of paretic leg muscles in man, allowing feedback–controlled movements to be generated from the wrist" J. Physiol. 343:20–21.

Rebersek, S., Stojnik, P. and Vodovnik, L (1971) "1.7 Position–controlled brace utilizing surface electrodes." In "Development of Orthotic Systems using functional electrical stimulation and myo– electric control". Progress Report, University of Ljubljana, Vodovnik, L., pp. 45–48, prepared for U.S. Dept. of Health Education and Welfare Social and Rehabilitation Service, under contract No. SRS– YUGO 23–68.

"Grays Anatomy, 36th Edition" 1980, Eds. Williams, P.L. and Warwick, R. Churchill Livingstone: London, pp 328–329.

Grays Anatomy, 36th Edition 1980, Eds. Williams, P.L. and Warwick, R. Churchill Livingstone: London, p. 1196.

\* cited by examiner

METHOD AND APPARATUS FOR CONTROLLING A DEVICE OR PROCESS WITH VIBRATIONS GENERATED BY TOOTH CLICKS

CROSS-REFERENCES TO RELATED APPLICATIONS

This application claims the benefit of U.S. Provisional Application No. 60/419,393, filed Oct. 17, 2002, and U.S. Provisional Application No. 60/421,633, filed Oct. 25, 2002, under 35 U.S.C. § 119(e).

FIELD OF THE INVENTION

The present invention relates to methods and apparatus for use in controlling a device or process, with particular regard for the needs of disabled persons.

BACKGROUND OF THE INVENTION

There has been a number of alternative technologies developed for controlling a device or process, for use by disabled persons. While these technologies need not be used solely by disabled persons, they have been developed with the particular physical limitations of disabled persons in mind. U.S. Pat. No. 5,233,662 (Christensen 1993) and U.S. Pat. No. 5,523,745 (Fortune et al 1996) describe tongue operated apparatus. U.S. Pat. No. 4,865,610 (Muller 1989) describes a mouthpiece into which signals are input by sucking or blowing. U.S. Pat. No. 5,812,978 (Nolan 1998) describes the use of a voice control apparatus.

The use of signals from switches or sensors to control functional electrical stimulation (FES) of paralyzed muscles is known. Use of a shoulder position sensor to control wrist extension via an implanted FES stimulator has been described (Vodovnik, L (1971) "Development of Orthotic Systems using functional electrical stimulation and myo-electric control," Progress Report, University of Ljubljana, prepared for U.S. Dept. of Health Education and Welfare Social and Rehabilitation Service, under contract No. SRS-YUGO 23-68). Use of contact switches placed in the shoe to control FES of the leg muscles has been described (Liberson W. T., Holmquest H. J. Scott D, Dow, M. (1961) "Functional electrotherapy: stimulation of the peroneal nerve synchronized with the swing phase of the gait of hemiplegic patients."

Archives of Physical and Medical Rehabilitation 42: 101–105). Shoulder sensors have also been used to control hand opening and pinch-grip (Peckham, P. K, Marsolais, E. B. & Mortimer, J. T. (1980) J. Hand Surgery, 5,462–469; Petrovsky, J. S. (1985) Hand Control System, EP-145504-A, CA1263446-A, U.S. Pat. No. 4,558,704; Peckham, P. H. & Keith, M. W. (1992) "Motor prostheses for restoration of upper extremity function" In "Neural Prostheses: Replacing Motor Function After Disease or Disability" eds.: Stein, R. B., Peckham, P. H. & Popovic, D. B. New York: Oxford University Press. A wrist position sensor has been used to control FES of leg muscles (Prochazka, A. & Wiles, C. M. (1983) "Electrical stimulation of paretic leg muscles in man, allowing feedback-controlled movements to be generated from the wrist" J. Physiol. 343, 20P). A switch mounted on a watch band has been used to trigger FES-evoked pinch-grip (Handa, Y., Itchie, M, Handa, T., Takahashi, K Saito, C., Kameyama, J. & Hoshimiya, N. (1989) "FES-control of multi-joint system in the paralysed upper limb." Osaka Int. Workshop on FNS. pp. 91–95.). A multi-component device in which wrist position sensors are used to stimulate FES evoked pinch-grip has also been described (Crago, P. E., Peckham, P. H., Mansour, J. M., Lan, N., Kilgore, K. and Chizeck, H. J. (1991) a, b, c,) "Functional neuromuscular stimulation for restoration of hand grasp." NIH Contract NO1-NS-9-2356 7th, 8th & 9th Progress Reports, June, September & December, 1991; Crago, P. E., Peckham, P. H. Mansour, J. M., Lan, N., Kilgore, K. and Chizeck, H. J. (1992). "Functional neuromuscular stimulation for restoration of hand grasp." NIH Contract NO1-NS-9-2356. 10th, 11th & 12th Progress Reports, March, June, September, 1992; Peckham, P. H. & Keith, M. W. (1992) "Motor prostheses for restoration of upper extremity function" In: Neural Prostheses: Replacing Motor Function After Disease or Disability, eds.: Stein, R. B., Peckham, P. H. 8c Popovic, D. B. New York: Oxford University Press). An FES garment is described (Prochazka, A., Wieler, M. Kenwell, Z. & Gauthier M. J. (1996) U.S. Pat. No. 5,562,707 in which FES is controlled by signals from proximity detectors which transduce relative motions of an adjacent limb segment such as the hand by monitoring changes in electric or magnetic fields, or changes in the intensity of sound or light transmitted from the adjacent limb segment or changes in the stretching of skin underlying the garment.

SUMMARY OF THE INVENTION

The present invention is an alternative method and apparatus for controlling a device or process, which has been developed primarily with a view to accommodating the needs of disabled persons.

According to one aspect of the present invention there is provided a method for use in controlling a device or process. A first step involves attaching a detector to a person's head. A second step involves detecting mechanical vibrations elicited by sudden contact of upper and lower teeth. A third step involves using the mechanical vibrations to trigger a signal to control operation of a device or process.

According to another aspect of the present invention there is provided an apparatus for use in controlling a device or process, which includes a detector adapted to detect mechanical vibrations elicited by sudden contact of upper and lower teeth. A means is provided for securing the detector to a person's head. A means is provided for transmitting data from the detector to a controller that controls a device or process. The controller may be physically connected to the detector or separated from it.

With the method and apparatus, as described above, a sudden impact between the upper and lower teeth is used as a method of control. Once the basic functioning of the invention is understood there are various features which can be added in order to enhance or ensure the intended functioning of the invention.

In order to ensure signals are not triggered accidentally, the detector may be equipped with an electronic filter and or a logic circuit which screens out incidental teeth contact which may occur during talking or eating.

In order to communicate with the controller, a signal corresponding to the time of contact may be transmitted either by wires or by a wireless transmitter to the controller.

The sensor used in the detector can take a number of forms. Beneficial results have been obtained through the use of an accelerometer or microphone.

The detector may be attached at different positions on a person's head. Beneficial results have been obtained by positioning the detector over the bony mastoid process behind the ear. Beneficial results have also been obtained when the detector overlies the temporomandibular (jaw) joint.

In another embodiment the detector and transmitter could be in the form of a small encapsulated device implanted under the skin.

There are various means by which good contact can be made between the detector and the head of the person. This can be accomplished by providing the detector with an adhesive surface or by taping the detector to the skin or by wearing an elastic headband over said detector or by wearing a springy headpiece of the type used in earphones over said detector or by wearing glasses with springy arms that push said detector onto the skin behind the ear.

There are various technologies which can be used to permit wireless communication of the detector with the controller, such as acoustic or electromagnetic technologies. Data could also simply be transferred from the device to the controller by a cable. The detector component of the transmission system can also be a passive device such as a transponder.

There are various uses which can be made of the apparatus. The controller can be used to cause part of the body of the person wearing the detector to move. The controller can trigger such movement by stimulating muscles, stimulating nerves, controlling an active orthosis or controlling a prosthesis. The device or process being controlled need not be on the person. The device or process can be physically separated from the person wearing the detector. The detector can be used with a transmitter and a controller having a receiver to communicate information or control signals to other people or to electronic systems such as computers. It is possible that any one of a plurality of devices may be triggered according to the temporal pattern or the intensity of the detected vibrations.

BRIEF DESCRIPTION OF THE DRAWINGS

These and other features of the invention will become more apparent from the following description in which reference is made to the appended drawings, the drawings are for the purpose of illustration only and are not intended to in any way limit the scope of the invention to the particular embodiment or embodiments shown, wherein:

FIG. 1 is a side elevation view of a person wearing an apparatus fabricated in accordance with the teachings of the present invention, with the apparatus being used to operate an electronic stimulator built into a cuff worn on the user's forearm. The detector attached to the side of the user's head is provided with a vibration sensor and an electronic amplifier. Additionally it may be provided with a radio transmitter that may have its own portable power source such as a battery, or it may be in the form of a transponder, receiving power from a remote receiving device. The cuff is provided with electrodes that conduct electrical current into the users body, the purpose of which is to stimulate muscles to produce a movement. The electronic device attached to the cuff receives signals from the detector and uses the information therein contained to trigger the onset of trains of stimulating pulses delivered through the electrodes.

DETAILED DESCRIPTION OF THE PREFERRED EMBODIMENT

The preferred method and associated apparatus for controlling a device or process will now be described with reference to FIGS. 1 through 7.

Figure 1:
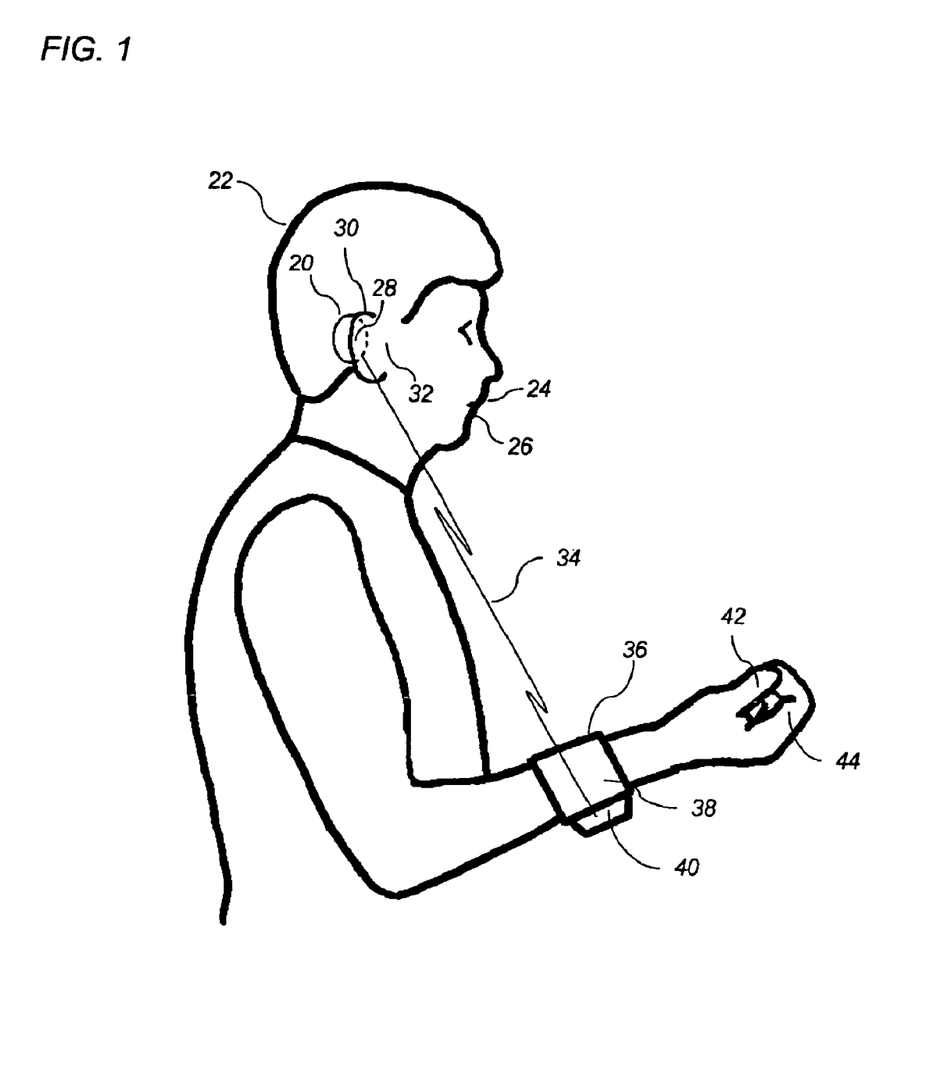
Figure 2:
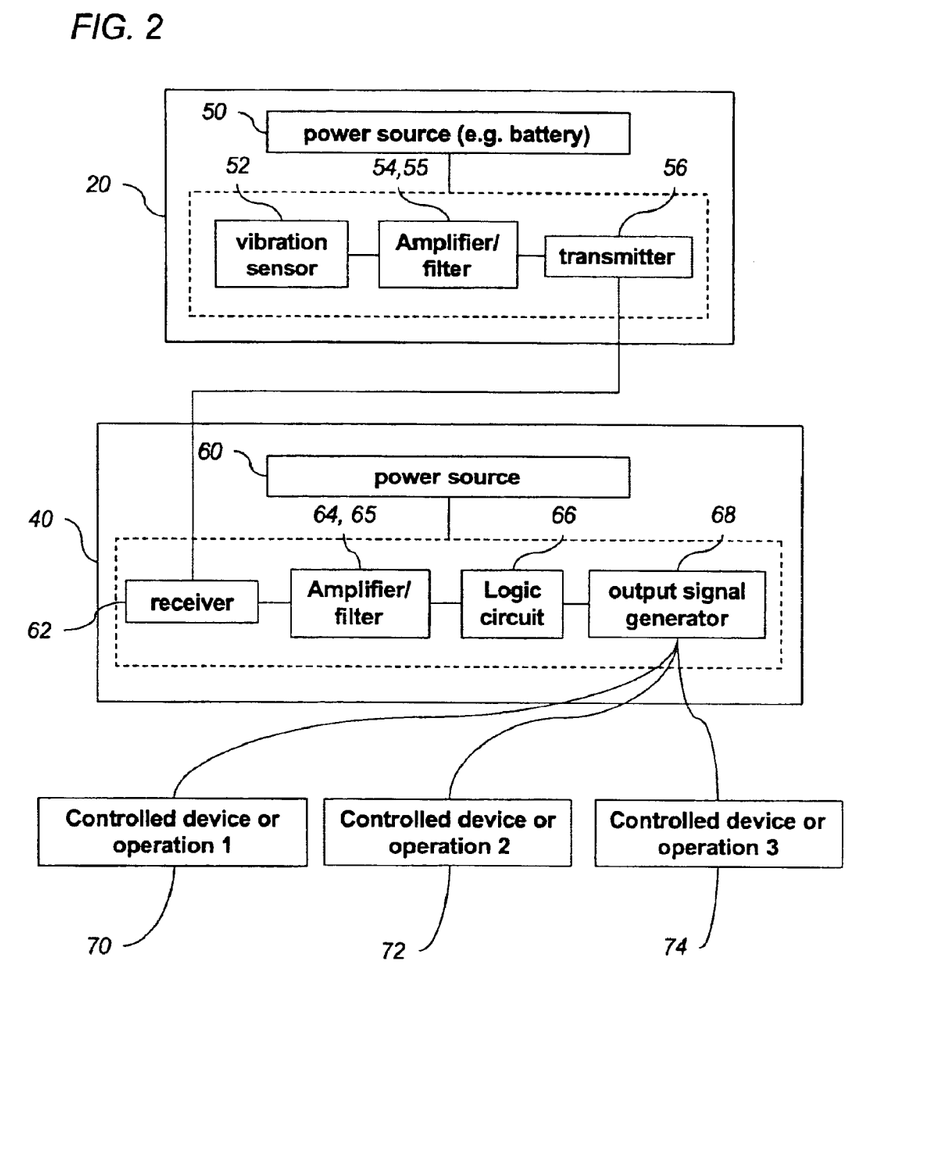
FIG. 2 is a schematic showing components of one embodiment of the apparatus. The top panel represents the detector and associated circuitry attached to the user's head. The middle panel represents the radio receiver part of the controller, which also incorporates an amplifier and filter that attenuates components of the response of the detector that are unrelated to the desired tooth contact signal (e.g. vibrations elicited by the user's speech). The bottom panel represents controlled devices such as the muscle stimulator in FIG. 1.
Figure 3:
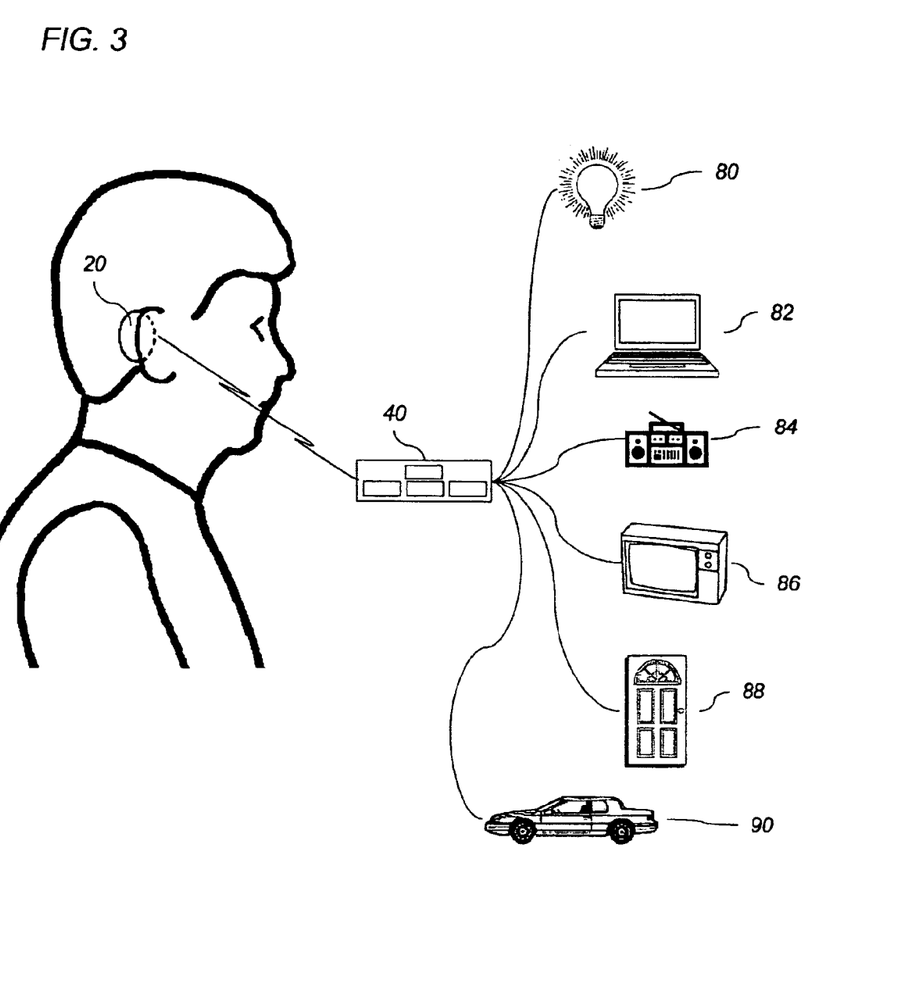
FIG. 3 is a side elevation view of a person wearing an apparatus fabricated in accordance with the teachings of the present invention, with the apparatus being used to control a plurality of devices.

Structure and Relationship of Parts:

Referring to FIG. 1, apparatus 10 includes a detector 20 which is secured to a person's head 22 by adhesive, adhesive tape or other suitable means. It should be noted that the preferred positioning of detector 20 is over a bony mastoid process 28 behind the person's ear 30 or overlying the person's temporomandibular (jaw) joint 32. Detector 20 is adapted to detect mechanical vibrations in head 22 caused by sudden contact of upper teeth 24 and lower teeth 26. Referring to FIG. 2, detector 20 is provided with a vibration sensor 52, such as an accelerometer or a sensitive microphone. It is preferred that a 3-axis accelerometer be used to maximize the selectivity of the detector to vibrations evoked by tooth clicks. In a preferred embodiment, detector 20 is provided with a power source 50, such as a battery or an electronic circuit, which can receive and store power transmitted electromagnetically. However, it will be understood that a passive device, such as a passive transponder may also be used. The preferred version of detector 20 also incorporates an electronic amplifier 54 that amplifies the fluctuations in voltage produced by the vibration sensor 52 in response to vibrations. Preferably, it is also provided with a filter 55 that selectively attenuates signals corresponding to vibrations unrelated to tooth contact. Referring to FIG. 1, FIG. 2 and FIG. 3, there is also included an electronic controller 40, with power source 60 that responds to certain states of the amplified and filtered vibration sensor signals by transmitting commands to one or more controlled devices, such as muscle stimulator cuff 36 in FIG. 1, other devices and operations exemplified by (but not limited to) 70, 72 and 74 in FIG. 2 and devices, such as: lights 80, computer 82, radio 84, television 86, door opener 88, automobile 90 in FIG. 3. The controller 40 may be physically separate from detector 20, as shown for example in FIGS. 1 and 2. In this case, detector 20 may be connected to controller 40 via physical links such as wire or fibre-optic cables. Alternatively, detector 20 may be equipped with a transmitter 56 that transmits the vibration-related signals 34 via an electromagnetic or acoustic communications method to a receiver 62 that is part of controller 40. The received signal is amplified by a signal amplifier 64 and filter 65. It may be further processed by a logic circuit 66 and an output signal generator 68 to control a plurality of devices 70, 72, 74 as shown in FIG. 1 and FIG. 2 and further elaborated in FIG. 3. Illustrated in FIG. 1, is an application relating to muscle stimulation. The person wears a cuff 36 with an in-built control circuit 40 connected to electrodes 38 within the cuff. As illustrated in FIG. 2, the control circuit 40 includes a radio receiver 62, a signal amplifier and filter 64 and 66. Control circuit 40 may also include a logic circuit 66 to maximize the selected recognition of tooth click related components of the signal and to derive command signals accordingly. The command signals are converted to trains of electrical current pulses by signal generator 68, which are transmitted to the muscles through electrodes 38 to activate muscles in the forearm that move the thumb 42 and fingers 44. The diversity of devices which may be controlled is further illustrated in FIG. 3 and includes as examples lights 80, computers 82, radios 84, television sets 86, electromechanically operated doors 88 and automobiles 90.

Figure 4:
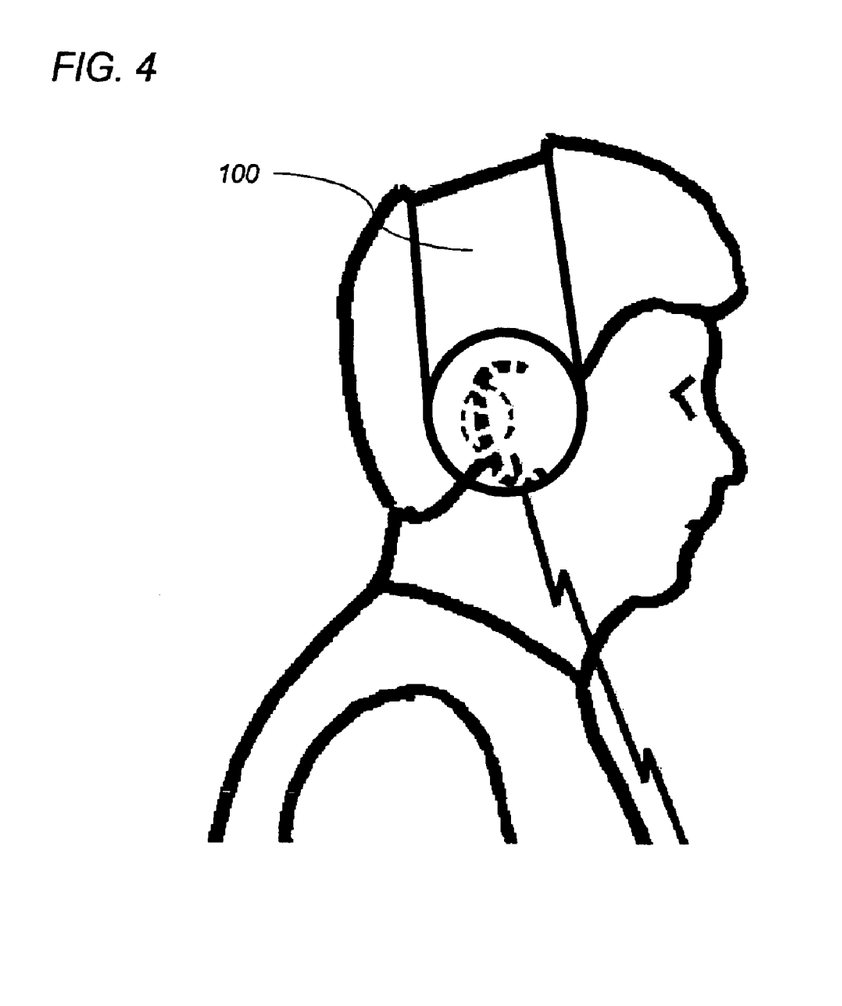
FIG. 4 is a side elevation view of a person wearing a version of the present invention in which the detector is pressed against the side of the head by a springy band such as is used in earphones.
Figure 5:
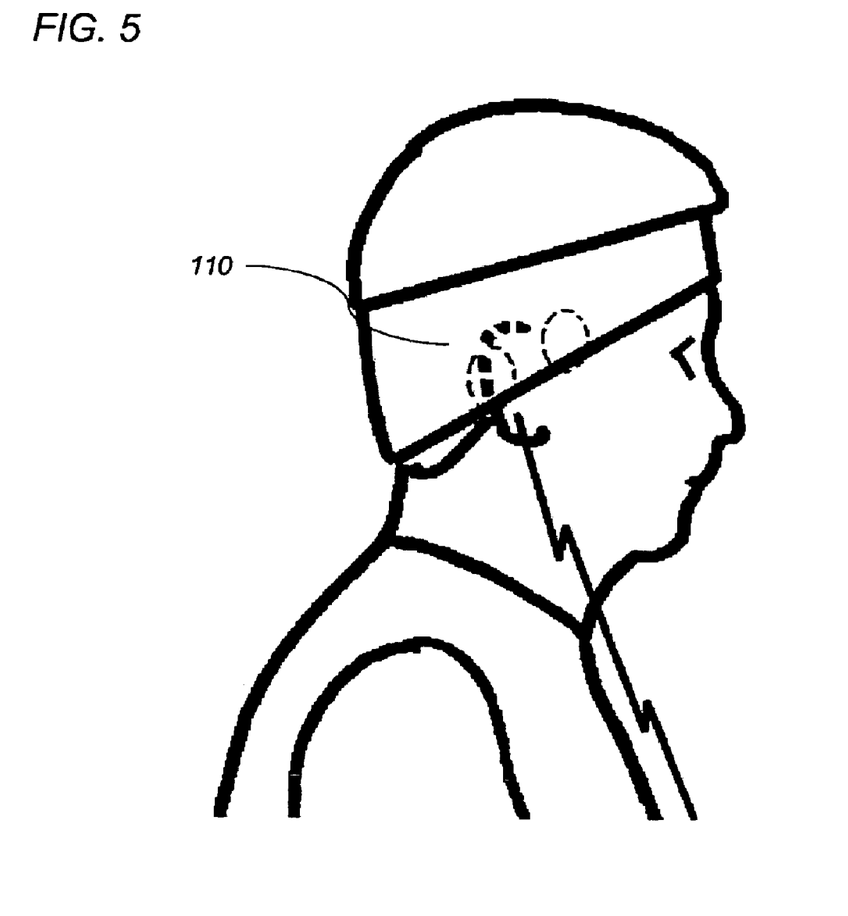
FIG. 5 is a side elevation view of a person wearing a version of the present invention in which the detector is pressed against the side of the head by an elastic headband.
Figure 6:
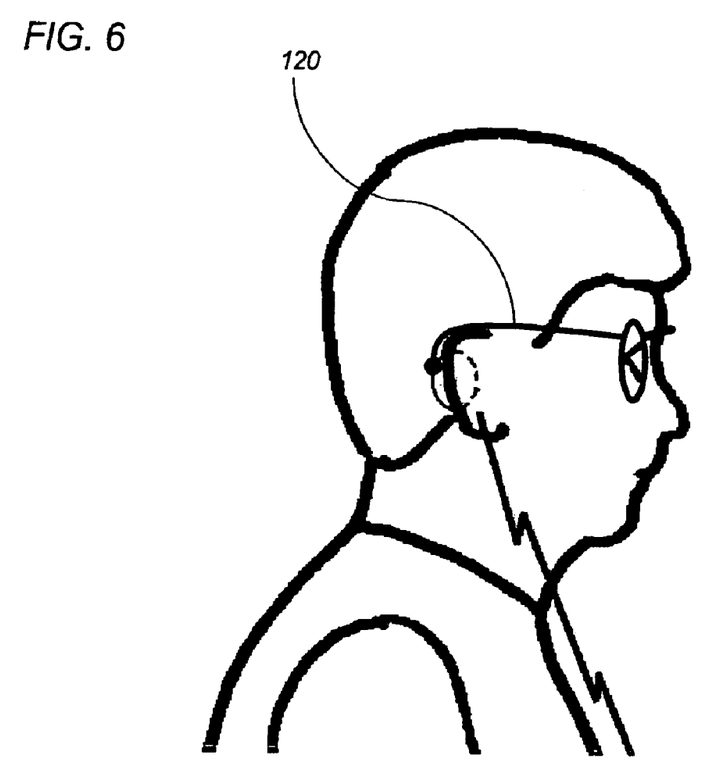
FIG. 6 is a side elevation view of a person wearing a version of the present invention in which the detector is pressed against the side of the head by one of the side-arms of a pair of glasses.
Figure 7:
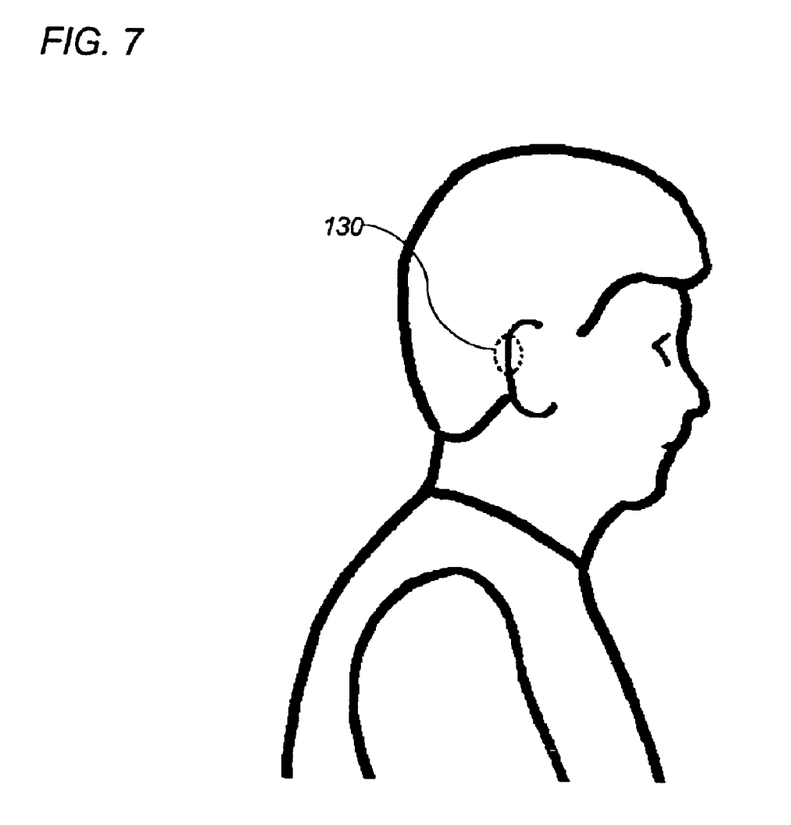
FIG. 7 is a side elevation view of a person wearing a version of the present invention in which the detector and transmitter are in the form of an encapsulated device implanted under the skin.

Means are provided to maintain a firm contact between the sensor and the user's head, to ensure good transmission of the vibrations caused by tooth contact to the sensor. Such means are exemplified in FIGS. 4, 5 and 6. FIG. 4 shows a spring-loaded headpiece 100, such as those used in earphones. FIG. 5 shows an elastic headband 110. FIG. 6 shows the detector 20 attached to a pair of spectacles 120 having springy arms. FIGS. 4, 5 and 6 are examples of three means of fixation, but it is understood that fixation is not limited to these means.

Operation:

The user dons the apparatus which in the preferred embodiment of FIG. 1 comprises the detector 20 and cuff 36 which includes controller 40 and electrodes 38. When power is switched on, either by a manual switch, or by a contact built into the apparatus, the user then controls the stimulator 40 by clicking his or her upper teeth 24 and lower teeth 26 together. Detector 20 and controller 40 respond to the vibrations elicited by the sharp contact between the teeth. The size and/or temporal features of the signals can be used to select between devices or operations. In the preferred embodiment of FIG. 1 successive tooth clicks are used as triggers to electrodes 38 which stimulate muscles to alternatively open and close thumb 42 and fingers 44 of the hand.

Variations:

As shown in FIG. 3, the device controlled can be a computer 82 or a plurality of other controlled devices 80, 84, 86, 88, 90. Other examples of coding to select between a plurality of devices or operations include double-clicks, multiple clicks, variable-intervals between clicks, and clicks of different amplitudes. Detector 20 could be used to operate a communications device in which coded information is transmitted from the user to another person or persons, i.e. telecommunication. In yet another embodiment the detector 20 and transmitter 56 are in the form of a small encapsulated device implanted under the skin 130 in the vicinity of the skull or temporomandibular joint, FIG. 7.

Cautionary Warnings:

Frequent sharp impact between the upper and lower teeth could eventually cause dental problems. Users should learn to generate minimal amplitude tooth clicks compatible with reliable detection by the apparatus.

The embodiments of the invention in which an exclusive property or privilege is claimed are defined as follows:

1. A method for assisting a person in controlling one or more devices, comprising the steps of:
   a) attaching a vibration sensor, capable of detecting mechanical vibrations, either
      i. to the person's head; or
      ii. under the skin over a bony mastoid process or over a temporomandibular joint;
   b) providing one or more devices capable of causing or stimulating movement of a body part of the person;
   c) detecting with the sensor, mechanical vibrations elicited by sudden contact of the person's upper teeth and lower teeth;
   d) generating an electrical signal from the sensed mechanical vibrations; and
   e) transmitting the electrical signal to the one or more devices to be controlled so as to cause or stimulate movement of the person's body part.

2. The method according to claim 1, wherein the sensor is an accelerometer.

3. The method according to claim 2, wherein steps, (c), (d), and (e) take place in an encapsulation under the skin.

4. The method according to claim 1, wherein the device being controlled is one capable of stimulating muscles or nerves, or is an active orthosis or prosthesis.

5. The method according to claim 4, wherein the sensor is attached on a side of the person's head.

6. The method according to claim 4, wherein the sensor is attached to the person's head over a bony mastoid process or over a temporomandibular joint.

7. The method according to claim 6, wherein the sensor is an accelerometer or a microphone.

8. The method according to claim 6, wherein the sensor is an accelerometer.

9. The method according to claim 8, wherein the sensor is attached to the person's head for detecting the vibrations using one or more attachment devices selected from the group consisting of an adhesive, an adhesive tape, an elastic headband, a spring loaded headpiece, and a pair of glasses with springy arms.

10. The method according to claim 9 or 3, wherein in step (e) the electrical signal is transmitted to an electronic controller adapted to produce an output signal to control the one or more devices.

11. The method according to claim 10, wherein the device being controlled is a cuff equipped with electrodes that stimulate muscles in the person's hand.

12. The method according to claim 4, wherein the sensor is attached to the person's head at a location to sense the mechanical vibrations of the person's bony mastoid process.

13. The method according to claim 4, wherein the sensor is attached to the person's head at a location to sense the mechanical vibrations of the person's temporomandibular joint.

14. The method according to claim 1, wherein the device being controlled is a cuff capable of stimulating the muscles in the person's hand.

15. The method according to claim 11, wherein the controller discriminates a temporal pattern or intensity from the electrical signal, and generates a corresponding output signal to control the one or more devices.

16. The method according to claim 15, further comprising amplifying the electrical signal.

17. The method according to claim 16, further comprising filtering the electrical signal to attenuate signals corresponding to vibrations unrelated to tooth clicks.

18. The method according to claim 17, wherein the controller includes a logic circuit to recognize selectively tooth click related components of the electrical signal.

19. The method according to claim 18, wherein the output signal is directed to a signal generator that generates trains of electrical pulses operative to stimulate muscles or nerves.

20. The method according to claim 19, wherein in step (e) the electrical signal or the output signal is transmitted using a wire, wireless or fibre optic transmitter or a passive transponder, and wherein the controller includes a receiver capable of receiving the transmitted electrical signal.

21. An apparatus for use with one or more devices, comprising:
a vibration sensor capable of detecting mechanical vibrations elicited by sudden contact of the person's upper teeth and lower teeth and of generating an electrical signal from the sensed mechanical vibrations for transmitting to the one or more devices; and either:
  i. an attachment device for attaching the vibration sensor to the person's head for detecting the mechanical vibrations; or
  ii. an encapsulation of the sensor for placement under the skin over a bony mastoid process or over a temporomandibular joint;
wherein the one or more devices being controlled is capable of causing or stimulating movement of a body part of the person.

22. The apparatus according to claim 21, wherein the sensor is an accelerometer.

23. The apparatus according to claim 22, further comprising means for transmitting the electrical signal to the one or more devices, and wherein when the apparatus includes an encapsulation of the sensor for placement under the skin, the encapsulation further encapsulating the means for transmitting the electrical signal.

24. The apparatus according to claim 23, wherein the means for transmitting is a wireless transmitter or a passive transponder, and wherein the electronic controller includes a receiver capable of receiving the transmitted electrical signal.

25. The apparatus according to claim 21, wherein the device being controlled is one capable of stimulating muscles or nerves, or is an active orthosis or prosthesis.

26. The apparatus according to claim 25, wherein the attachment device is adapted to attach the sensor on a side of the person's head.

27. The apparatus according to claim 25, wherein the attachment device is adapted to attach the sensor to the person's head over the bony mastoid process or over the temporomandibular joint.

28. The apparatus according to claim 26, wherein the sensor is an accelerometer or a microphone.

29. The apparatus according to claim 27, wherein the sensor is an accelerometer.

30. The apparatus according to claim 29, which further comprises means for transmitting the electrical signal to the one or more devices to be controlled.

31. The apparatus according to claim 30, wherein the attachment device is selected from the group consisting of an adhesive, an adhesive tape, an elastic headband, a spring loaded headpiece, and a pair of glasses with springy arms.

32. The apparatus according to claim 31 or 23, which further comprises an electronic controller adapted to receive the transmitted electrical signal and to produce an output signal to control the one or more devices.

33. The apparatus according to claim 32, wherein the device being controlled is a cuff equipped with electrodes that stimulate muscles in the person's hand.

34. The apparatus according to claim 25, wherein the attachment device is adapted to attach the sensor to the person's head at a location to sense the mechanical vibrations of the person's bony mastoid process.

35. The apparatus according to claim 25, wherein the attachment device is adapted to attach the sensor to the person's head at a location to sense the mechanical vibrations of the person's temporomandibular joint.

36. The apparatus according to claim 21, wherein the device being controlled is a cuff capable of stimulating the muscles in the person's hand.

37. The apparatus according to claim 33, wherein the controller discriminates a temporal pattern or intensity from the electrical signal, and generates a corresponding output signal to control the one or more devices.

38. The apparatus according to claim 37, further comprising an amplifier for amplifying the electrical signal.

39. The apparatus according to claim 38, further comprising a filter for filtering the electrical signal to attenuate signals corresponding to vibrations unrelated to tooth clicks.

40. The apparatus according to claim 39, wherein the controller includes a logic circuit to recognize selectively tooth click related components of the electrical signal.

41. The apparatus according to claim 40, wherein the output signal is directed to a signal generator that generates trains of electrical pulses operative to stimulate muscles or nerves.

42. The apparatus according to claim 41, wherein the means for transmitting is a wire, wireless or fibre optic transmitter or a passive transponder, and wherein the controller includes a receiver capable of receiving the transmitted electrical signal.

* * * * *

UNITED STATES PATENT AND TRADEMARK OFFICE
CERTIFICATE OF CORRECTION

PATENT NO. : 6,961,623 B2
DATED : November 1, 2005
INVENTOR(S) : A. Prochazka It is certified that error appears in the above-identified patent and that said Letters Patent is hereby corrected as shown below:

Column 7,
Line 45, "claim 26," should read -- claim 27, --.

Signed and Sealed this

Fourteenth Day of March, 2006

JON W. DUDAS
*Director of the United States Patent and Trademark Office*